(12) United States Patent
Miyamura

(10) Patent No.: US 8,927,228 B2
(45) Date of Patent: Jan. 6, 2015

(54) REAGENT FOR BLOOD CELL COUNTING AND BLOOD ANALYSIS METHOD

(71) Applicant: HORIBA, Ltd., Kyoto (JP)

(72) Inventor: Kazuhiro Miyamura, Amagasaki (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 14/033,221

(22) Filed: Sep. 20, 2013

(65) Prior Publication Data

US 2014/0017719 A1  Jan. 16, 2014

Related U.S. Application Data

(63) Continuation of application No. 13/467,840, filed on May 9, 2012.

(30) Foreign Application Priority Data

May 10, 2011  (JP) .................. 2011-105611

(51) Int. Cl.
G01N 33/50 (2006.01)
G01N 33/49 (2006.01)
G01N 15/12 (2006.01)
G01N 1/38 (2006.01)
G01N 15/10 (2006.01)

(52) U.S. Cl.
CPC ............ G01N 33/5094 (2013.01); G01N 33/49 (2013.01); G01N 15/12 (2013.01); G01N 1/38 (2013.01); G01N 2015/1006 (2013.01)
USPC .......................................... 435/29

(58) Field of Classification Search
USPC .......................................... 435/29
See application file for complete search history.

(56) References Cited

U.S. PATENT DOCUMENTS 4,529,705 A * 7/1985 Larsen .................. 436/17

FOREIGN PATENT DOCUMENTS

| CA | 1222679 A | 6/1987 |
| JP | 03144364 A | 6/1991 |
| WO | 8404969 A1 | 12/1984 |

OTHER PUBLICATIONS

Jancinova et al., On the Inhibitory Effect of Chloroquine on Blood Platelet Aggregation, Thrombosis Research, vol. 74, No. 5, pp. 495-504, Jun. 1, 1994.*
Casabianca, Leah B., et al. "Antimalarial Drugs and Heme in Detergent Micelles: An NMR Study", Journal of Inorganic Biochemistry, vol. 103, No. 5, May 2009, pp. 745-748.
European Patent Office, European Search Report if European Patent Application No. 12167421, Munich, Germany, Jun. 22, 2012, 3 pages.
Jancinova, V. et al., "On the Inhibitory Effect of Chloroquine on Blood Platelet Aggregation," Thrombosis Research vol. 74, No. 5, Jun. 1994, pp. 495-504.

* cited by examiner

*Primary Examiner* — Karen Cochrane Carlson
*Assistant Examiner* — Jennifer M. H. Tichy
(74) *Attorney, Agent, or Firm* — Marvin A. Motsenbocker; Mots Law, PLLC

(57) ABSTRACT

Disclosed is a novel reagent for blood cell counting and a novel blood analysis method, which enable blood cells such as leukocytes to be counted with high accuracy by dissociating platelet aggregates in capillary blood collected from a living body. The reagent for blood cell counting is used to dilute capillary blood collected from a living body to prepare a blood sample in order to count blood cells in the collected capillary blood using a particle analyzer, and is an aqueous solution containing a chloroquine salt.

14 Claims, 9 Drawing Sheets

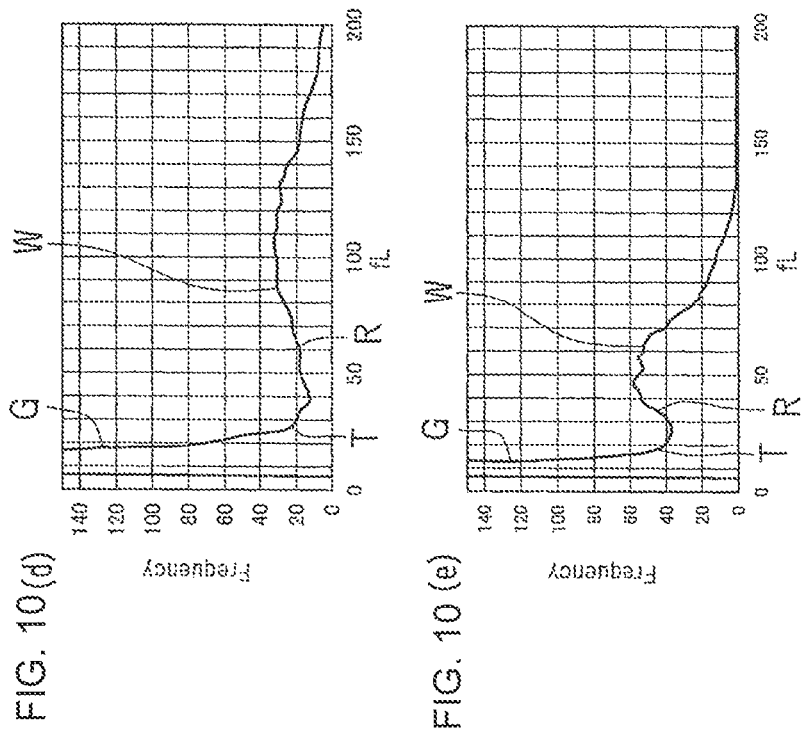
FIG. 10(d)
FIG. 10(e)
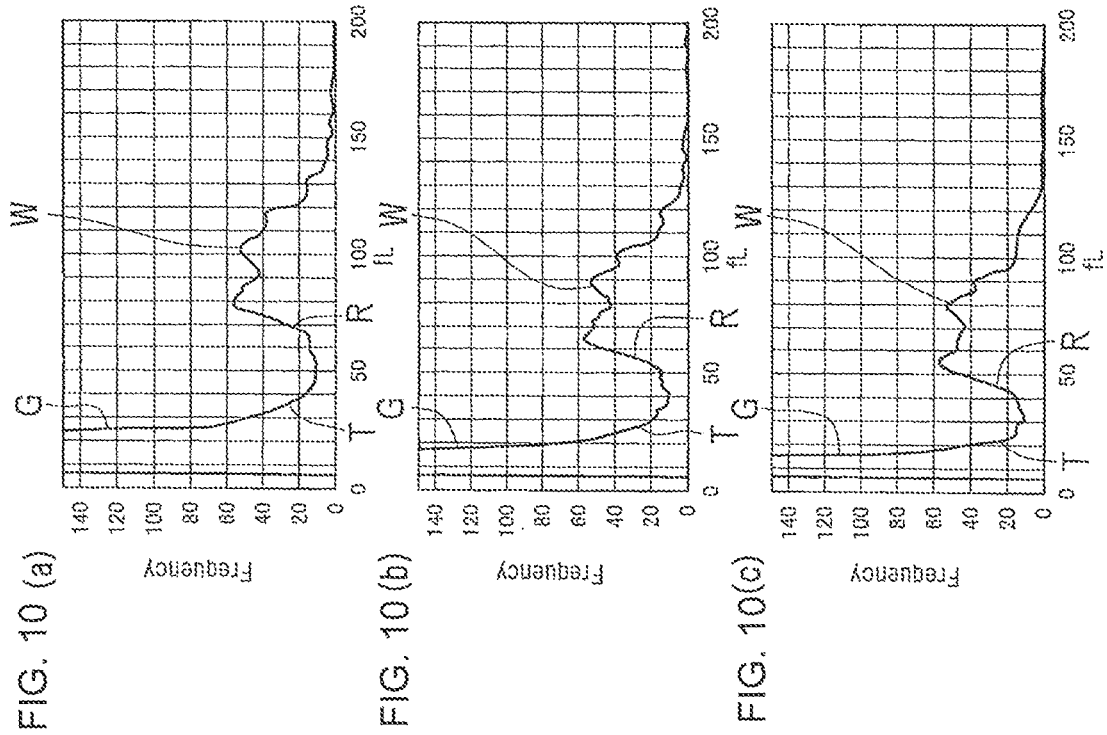
FIG. 10(a)
FIG. 10(b)
FIG. 10(c)

US 8,927,228 B2

REAGENT FOR BLOOD CELL COUNTING AND BLOOD ANALYSIS METHOD

CROSS-REFERENCE TO RELATED APPLICATIONS

This application is a continuation of U.S. patent application Ser. No. 13/467,840, entitled REAGENT FOR BLOOD CELL COUNTING AND BLOOD ANALYSIS METHOD, filed on May 9, 2012, which in turn claims, under 35 USC 119(a), priority based on Japanese Patent Application No. 2011-105611, filed on May 10, 2011. The entire disclosures of both applications are incorporated herein by reference in their entirety for all purposes.

TECHNICAL FIELD

The present invention relates to a reagent for blood cell counting, which is mixed with capillary blood collected from a living body, and to a blood analysis method of counting blood cells in capillary blood collected from a living body using a particle analyzer.

BACKGROUND ART

Conventionally, a particle analyzer which uses an analysis method called "flow cytometry" is used as a means for counting blood cells in blood.

In the process of counting erythrocytes in blood, collected blood is diluted with physiological saline to prepare a blood sample, and the blood sample is introduced into a particle analyzer, in which particles having a specific volume range (e.g., 36-60 femtoliter (fL=$10^{-15}$ liter)) are then counted one by one. At this time, leukocytes having a volume almost equal to that of erythrocytes are also counted, but the error caused by counting leukocytes is negligible because the concentration of leukocytes in blood is generally about 0.1-0.2% based on the concentration of erythrocytes.

In contrast, in the process of counting leukocytes in blood, collected blood is diluted with a hemolytic reagent to prepare a blood sample, and the blood sample is introduced into a particle analyzer, in which particles having a specific volume range (e.g., about 25 to 450 fL) are then counted one by one. The hemolytic reagent contains a component that breaks the membrane of blood cells. Because erythrocytes have no nucleus, when the membrane of the erythrocytes is broken, hemoglobin is released and the erythrocytes lose their shape or size, and thus are lysed. On the other hand, because the leukocytes have a nucleus, these cells are lysed to leave bare nuclei (particles) which are then dispersed in the blood sample. Accordingly, leukocytes can be counted by introducing a blood sample containing lysed erythrocytes into a particle analyzer and counting particles having a specific volume range in the particle analyzer.

Methods of collecting blood from a living body in blood testing include two methods: a method of collecting venous blood from a subcutaneous vein; and a method of collecting capillary blood from a fingertip or an earlobe.

In the case in which a blood sample obtained by diluting venous blood with a hemolytic reagent is analyzed in a particle analyzer, as shown in the leukocyte volume histogram of FIG. 11, the noise derived from the debris of lysed platelets or erythrocytes (ghost "G") and the peak derived from leukocytes (leukocyte "W") are clearly distinguished from each other. Thus, leukocytes can be counted with relatively high accuracy.

Because collection of venous blood is performed by inserting a syringe needle into a subcutaneous vein and collecting blood directly from the blood vessel, the aggregation of platelets immediately after blood collection is not generally admitted. In addition, collected venous blood is diluted with a hemolytic reagent containing ethylenediamine tetraacetate as an anti-aggregation agent (platelet anti-aggregation agent), and thus a means for inhibiting the aggregation of platelets in a blood sample is established (see, for example, Patent Document 1).

Patent Documents

Patent Document 1: Japanese Unexamined Patent Publication No. Hei 3-144364

DISCLOSURE OF THE INVENTION

Problems to be Solved by the Invention

However, in the case in which a blood sample obtained by diluting capillary blood with a hemolytic reagent is analyzed in a particle analyzer, as shown in the leukocyte volume histogram of FIG. 12, the tailing portion T of the ghost peak G and the leading portion R of the leukocyte peak W overlap with each other over a relatively wide range. For this reason, leukocytes cannot be counted with high accuracy. This is because platelet aggregates are miscounted over the range from the tailing portion T of the ghost peak G to the leading portion R of the leukocyte peak W.

Collection of capillary blood is performed by pricking a fingertip or an earlobe with a lancet to obtain a very small amount of blood and is advantageous in that blood can be collected in a simple and rapid manner. However, a tissue solution is likely to be incorporated into the blood being collected, and thus platelets may aggregate rapidly after collection.

Ethylenediamine tetraacetate has the function of inhibiting the aggregation of platelets, but does not have the function of dissociating platelet aggregates. Thus, even when capillary blood in which platelets aggregate rapidly after blood collection is treated with a hemolytic reagent containing ethylenediamine tetraacetate, platelet aggregates cannot be dissociated.

The present invention has been made in order to solve the above technical problem, and it is an object of the present invention to provide a novel reagent for blood cell counting and a blood analysis method, which enable blood cells such as leukocytes to be counted with high accuracy by dissociating platelet aggregates in capillary blood collected from a living body.

Means for Solving the Problems

The reagent for blood cell counting according to the present invention is used to dilute capillary blood collected from a living body to prepare a blood sample in order to count blood cells in the collected capillary blood using a particle analyzer, and is characterized in that it is an aqueous solution containing a chloroquine salt.

The reagent for blood cell counting according to the present invention is used to dilute "capillary blood" collected from a living body to prepare a blood sample in order to count blood cells such as leukocytes in the collected capillary blood using a "particle analyzer". As used herein, the term "capillary blood" means blood obtained by pricking a fingertip or an earlobe with a lancet (fingertip blood or earlobe blood). The term "particle analyzer" means a particle analyzer (flow cytometer or coulter counter) that uses an analysis method called flow cytometry in which fine particles are dispersed in a fluid which is then allowed to flow thinly while individual particles in the fluid are counted. The particle analyzer may be broadly divided into two types: one that uses an optical detection method in which light scattering or fluorescence is detected; and the other that uses an electrical resistance detection method in which a change in impedance when particles pass through a thin hole is detected. The electrical resistance detection method is superior in that it is simple and convenient.

The "chloroquine salt" that is contained in the reagent for blood cell counting according to the present invention serves to dissociate platelet aggregates in capillary blood and refers to a compound having a quinoline backbone and containing a chloro group. Particularly, salts of chloroquinoline derivatives which have a chloro group introduced at position 7 of the quinoline backbone and an amino group introduced at position 4 of the quinoline backbone are preferably used in the present invention. Specific examples of the chloroquine salt include chloroquine diphosphate (7-chloro-4-[4-(diethylamino)-1-methylbutylamino]quinoline diphosphate), hydroxychloroquine sulfate (7-chloro-4-[4-N-ethyl-N-(2-hydroxyethyl)amino]-1-methylbutylamino)quinoline sulfate), and the like.

The reagent for blood cell counting according to the present invention preferably contains 10 g/L or more of the chloroquine salt.

In a conventional method of counting leukocytes, a dilution process of diluting blood collected from a living body about 100-500-fold with a reagent is carried out. It has been found that when a very small amount of a chloroquine salt is contained in a reagent, platelet aggregates can be dissociated by carrying out the dilution process using the reagent. With respect to the dissociation of platelet aggregates, the upper limit of the concentration of the chloroquine salt in the reagent is not specifically limited. However, as the concentration of the chloroquine salt increases, the cost of the reagent increases. For this reason, the upper limit of the concentration of the chloroquine salt is preferably limited to 100 g/L.

The reagent for blood cell counting according to the present invention preferably further contains a surfactant having hemolytic activity. As the surfactant, any surfactant may be used without particular limitation, so long as it breaks the membrane of blood cells when mixed with blood, and lyses erythrocytes in blood while lysing leukocytes to leave bare nuclei. The surfactant may be ionic or nonionic. The ionic surfactant is preferably an anionic surfactant. The anionic surfactant is preferably a quaternary ammonium salt. Specific examples of the quaternary ammonium salt include chlorides or bromides of hexadecyltrimethyl ammonium or dodecyltrimethyl ammonium. Meanwhile, specific examples of the nonionic surfactant include saponin.

Preferably, the reagent for blood cell counting according to the present invention contains a chloroquine salt such that it can dissociate platelet aggregates. In addition, the concentration of a surfactant in the reagent for blood cell counting is limited such that a leukocyte peak in a leukocyte volume histogram will be clear.

In this regard, the reagent for blood cell counting according to the present invention preferably contains 10-50 g/L of the surfactant.

It has been found that if the reagent for blood cell counting contains 10 g/L or more of the surfactant, it can break the membrane of blood cells when the dilution process is carried out using the reagent, and it can lyse erythrocytes in blood in the dilution step while lysing leukocytes to leave bare nuclei. On the other hand, if the concentration of the surfactant in the reagent for blood cell counting is more than 50 g/L, the volume of leukocytes in the blood sample will decrease. For this reason, the concentration of the surfactant in the reagent for blood cell counting according to the present invention is preferably set in the range of 10 to 50 g/L (more preferably 20 to 40 g/L).

In addition, the reagent for blood cell counting according to the present invention preferably further contains an "electrolyte" such that the osmotic pressure of the reagent is adjusted to 200-600 Osm/kg.

The "electrolyte" is not specifically limited, so long as it is ionized to cations, such as sodium ions, potassium ions or magnesium ions, and anions such as chloride ions, bromide ions or phosphate ions, when it is dissolved in water. Specific examples of the electrolyte include sodium chloride, sodium bromide, potassium chloride, potassium bromide, calcium chloride, calcium bromide, magnesium chloride, magnesium bromide, sodium phosphate, potassium phosphate, and the like.

If the concentration of the electrolyte in the reagent for blood cell counting is so low that the osmotic pressure of the reagent is less than 200 Osm/kg, the expansion and degradation of leukocytes will result. On the other hand, if the concentration of the electrolyte in the reagent for blood cell counting is so excessively high that the osmotic pressure of the reagent is more than 600 Osm/kg, the volume of leukocytes will decrease such that the leukocyte peak will shift to the lower volume side so as to approach the ghost peak. For this reason, according to the present invention, the osmotic pressure of the reagent for blood cell counting is preferably adjusted in the range of 200 to 600 Osm/kg (more preferably, 300 to 400 Osm/kg). In this case, the leukocyte peak can be prevented from being excessively close to the ghost peak.

Preferably, the reagent for blood cell counting according to the present invention is configured such that a minimum value of a relative frequency of valleys in distribution where the tailing portion of a ghost peak and the leading portion of a leukocyte peak in a leukocyte volume histogram, which is obtained when introducing the blood sample into the particle analyzer, overlap with each other lies within a particle volume range of 35 to 50 fL.

When the minimum value of the relative frequency of the valleys in the distribution where the tailing portion of the ghost peak and the leading portion of the leukocyte peak in the leukocyte volume histogram, which is obtained by counting leukocytes using the particle analyzer, overlap with each other lies within the particle volume range of 35 to 50 fL, a clear leukocyte peak can be obtained and the leukocyte peak can be prevented from being excessively close to the ghost peak, so that the miscounting derived from the platelet aggregates can be reduced. Thus, leukocytes in the blood sample can be counted with high accuracy.

In addition, the reagent for blood cell counting according to the present invention preferably further contains an "anti-aggregation agent".

As used herein, the term "anti-aggregation agent" means one having the property of inhibiting the aggregation of platelets. When the reagent for blood cell counting according to the present invention further contains the anti-aggregation agent, platelets (including platelets dissociated by the chloroquine salt) can be prevented from aggregating. Specific examples of the anti-aggregation agent include salts of ethylenediamine tetraacetate (EDTA), for example, EDTA-2Na (disodium salt), EDTA-2K (dipotassium salt), EDTA-3Na (trisodium salt) or EDTA-3K (tripotassium salt), heparin, acetylsalicylic acid, magnesium sulfate, etc. The concentration of the anti-aggregation agent in the reagent for blood cell counting is preferably 0.01-0.2 g/L, but is not specifically limited thereto.

The reagent for blood cell counting according to the present invention is preferably diluted with a buffer solution in order to stabilize the pH (hydrogen ion concentration) of the reagent. In addition, the reagent for blood cell counting according to the present invention may further contain a non-ionic surfactant for adjusting surface tension, a pH-adjusting agent for adjusting pH, a membrane protective agent for stabilizing bare nuclei remaining after lysis of leukocytes, a preservative for increasing storage stability, and other various additives.

Specific examples of the "buffer solution" include acetate buffer, phosphate buffer, citrate buffer, borate buffer, tartrate buffer, and tris buffer. Specific examples of the pH-adjusting agent include sodium hydroxide and hydrochloric acid.

The "nonionic surfactant" for adjusting surface tension is not specifically limited, so long as it contains a hydrophilic group and a hydrophobic group in the molecule and has the property of lowering the surface tension of the reagent for blood cell counting. Specific examples of the nonionic surfactant include "ether-type nonionic surfactants", such as polyoxyethylene decyl ether, polyoxyethylene lauryl ether, polyoxyethylene oleyl ether, polyoxyethylene octylphenyl ether or polyoxyethylene nonylphenyl ether; and ester-type nonionic surfactants (including etherester-type nonionic surfactants), such as polyoxyethylene lauric acid ester, polyoxyethylene oleic acid ester, polyoxyethylene sorbitan lauric acid ester, polyoxyethylene sorbitan oleic acid ester, sorbitan mono- (or di-)oleic acid ester, sorbitan mono- (or di-)lauric acid ester, or sorbitan mono- (or di-)isostearic acid ester.

Specific examples of the "preservative" include sodium azide, sodium omadine, Kathon CG, ROCIMA® 553, thimerosal and the like. Specific examples of the "membrane protective agent" include lower alcohols such as isopropyl alcohol, glutaraldehyde, dimethyl urea, glucose and the like.

The blood analysis method of the present invention is a blood analysis method in which blood cells such as leukocytes, which are contained in capillary blood collected from a living body, are counted in a particle analyzer, the blood analysis method comprising the steps of: collecting capillary blood from a living body; diluting the collected capillary blood with the reagent for blood cell counting according to the present invention to prepare a blood sample; and introducing the blood sample into the particle analyzer and counting leukocytes in the blood sample using the particle analyzer.

Preferably, in the blood analysis method of the present invention, the step of counting the leukocytes comprises determining a count start volume in a particle volume range of 35 to 50 fL and counting particles having a volume equal to or larger than the determined count start volume as leukocytes.

Counting of leukocytes in the particle analyzer is performed by considering particles having a specific range of volume in the blood sample as leukocytes, and counting the particles one by one. That is, the "count start volume" as used herein means the lower limit of the specific range of volume. In addition, the upper limit of the specific range in counting of leukocytes in the particle analyzer is the simple end point of the counting and is not a particularly important factor. In general, the upper limit of the specific range in the counting is about 300-500 fL.

Effect of the Invention

According to the present invention, platelet aggregates in capillary blood collected from a living body can be dissociated, and thus blood cells such as leukocytes can be counted with high accuracy using a particle analyzer.

BRIEF DESCRIPTION OF THE DRAWINGS

FIG. 3($b$) is a bottom view of the dilution bottle; FIG. 3($c$) is a sectional view showing a state in which a dilution bottle according to another embodiment is set with a bottle guide into a blood counter; FIG. 3($d$) is a partial sectional view showing another embodiment of the dilution bottle shown in FIG. 3($c$); and FIG. 3($e$) is a partial sectional view showing still another embodiment of the dilution bottle shown in FIG. 3($c$).

FIG. 7($c$) is a leukocyte volume histogram obtained by measuring a blood sample diluted with a reagent for blood cell counting according to Comparative Example 1.

FIGS. 9($d$) and 9($e$) are leukocyte volume histograms obtained by measuring blood samples diluted with reagents for blood cell counting according to Comparative Examples 2 and 3, respectively.

FIGS. 10($a$), 10($b$) and 10($c$) are leukocyte volume histograms obtained by measuring blood samples diluted with the inventive reagents for blood cell counting according to Examples 8, 1 and 9, respectively; and FIGS. 10($d$) and 10($e$) are leukocyte volume histograms obtained by measuring blood cells diluted with reagents for blood cell counting according to Comparative Examples 4 and 5, respectively.

EMBODIMENTS FOR CARRYING OUT THE INVENTION

Hereinafter, one embodiment of the present invention will be described, but is not intended to limit the scope of the present invention.

<Particle Analyzer>

A particle analyzer used in this embodiment was a micro blood cell counter (trade name (tentative name): Palm-LC; manufactured by Horiba Manufacturing Co., Ltd.).

—Measurement Unit 1—

Figure 1:
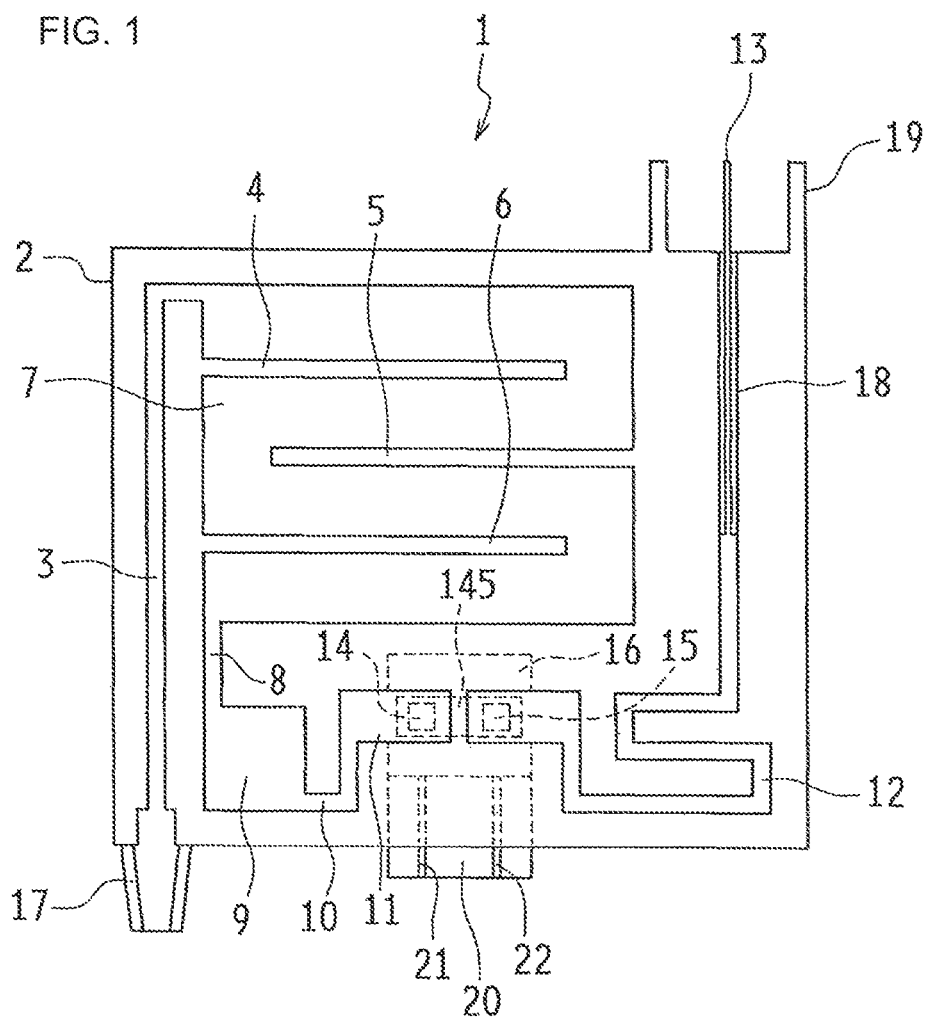
FIG. 1 is a top view showing a measurement unit in a micro blood cell counter.
Figure 2:
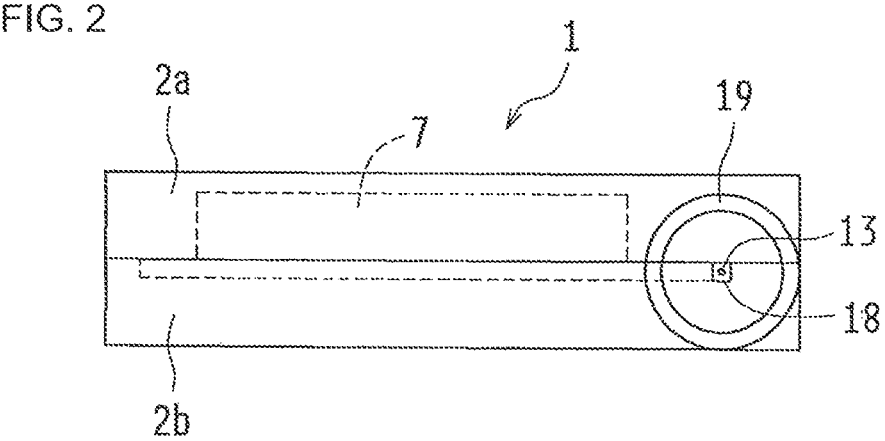
FIG. 2 is a side view showing a measurement unit in a micro blood cell counter.

FIGS. 1 and 2 show a measurement unit 1 in a micro blood cell counter. The measurement unit 1 is prepared in the form of a cartridge made of a resin such as polymethylmethacrylate (PMMA). A resin substrate 2 of the measurement unit 1 comprises: a fluid path 3 for connection to the outside, one end of which is connected to a pump connection port 17; a liquid storage cell 7 connected to the other end of the fluid path 3 and having fluid paths defined by walls 4, 5 and 6; an absorbance-measuring cell 9 connected to the liquid storage cell 7 through a fluid path 8; a detection fluid path 11 connected to the absorbance-measuring cell 9 through a fluid path 10; a capillary 13 connected to the detection fluid path 11 through a fluid path 12 having an approximately S-shape; and a sensor mounting portion 16 provided between the fluid path 10 and the fluid path 12.

Each of the elements formed on the resin substrate 2 has a predetermined depth and width. As shown in FIG. 2, the resin substrate 2 includes a resin substrate 2a and a resin substrate 2b. On the resin substrate 2a, the liquid storage cell 7 is formed with a depth of, for example, about 4 mm, and the absorbance-measuring cell 9 is also formed with a predetermined depth. On the resin substrate 2b, the fluid path 3 for connection to the outside, the fluid paths 8, 10 and 12, the detection fluid path 11 and a capillary-receiving fluid path 18 are formed with a width and depth of, for example, about 1 mm and about 1 mm, respectively. In addition, the sensor mounting portion 16 is formed on the resin substrate 2b. Moreover, the allocation of the fluid paths and other elements formed on the resin substrates 2a and 2b is not limited to the above, and the depth, width and the length of these elements may be allocated such that the resin substrates 2a and 2b can be effectively used.

After the elements are formed on the resin substrates 2a and 2b as described above, the resin substrate 2a and the resin substrate 2b are bonded to each other by means of, for example, an adhesive or a double-sided adhesive tape, so as to prevent liquid leakage. Subsequently, the capillary 13 made of, for example, glass, is buried in the capillary-receiving fluid path 18, and is fixed to the capillary receiving fluid path 18 by, for example, an adhesive, while the outer circumferential surface of the capillary 13 and the inner circumferential surface of the capillary-receiving fluid path are sealed.

Subsequently, the center of a bottle guide 19 is aligned with the center of the capillary 13. In this state, the bottle guide 19 is bonded to the end sides of the resin substrates 2a and 2b. In addition, the pump connection port 17 is connected to the fluid path 3 for connection to the outside 3, and in this state, the pump connection port 17 is bonded to the end sides of the resin substrates 2a and 2b. A sensor chip 145 is provided with electrodes 14 and 15 for detecting variation in the impedance of a blood sample. A sensor substrate 20 having the sensor chip 145 mounted thereon is attached to a sensor mounting portion 16 to provide a sensor unit, thereby completing the measurement unit 1 in this micro blood cell counter. The electrodes 14 and 15 are connected to lead lines 21 and 22, respectively, as the sensor chip 145 is mounted on the sensor substrate 20, whereby a signal in the sensor unit can be drawn from the lead lines 21 and 22. In the above description, the sensor chip 145 is attached to the sensor mounting portion 16 in a later step. However, the sensor chip 145 may be formed on the resin substrate 2a or 2b, before the electrodes 14 and 15 are attached to the sensor chip 145 by sputtering.

—Dilution Bottle 23—

Figure 3:
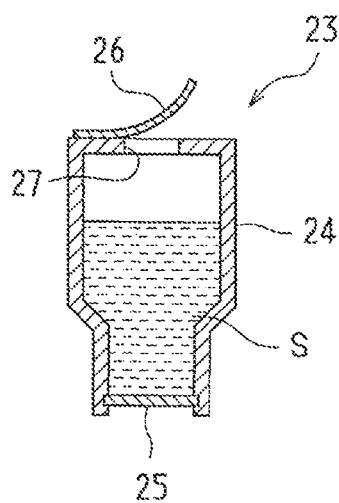
FIG. 3($a$) is a sectional view showing a dilution bottle in a micro blood cell counter.
Figure 3:
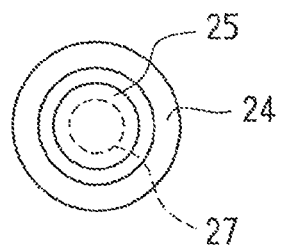
Figure 3:
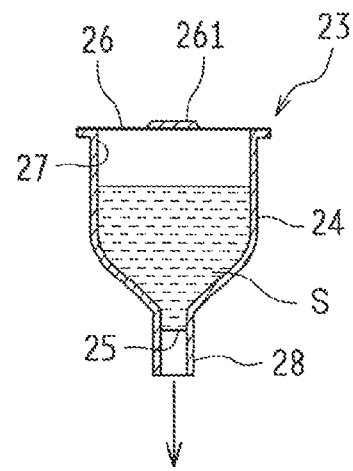
Figure 3:
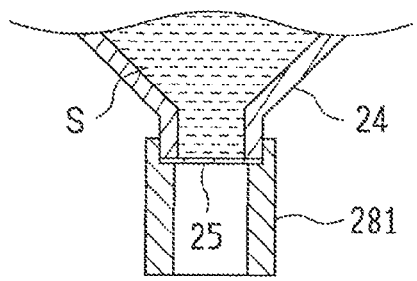
Figure 3:
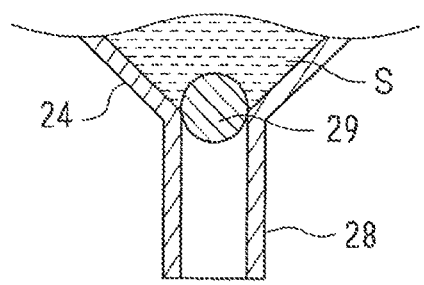

FIGS. 3(a) and 3(b) show a dilution bottle 23. The dilution bottle 23 comprises: a container 24 for receiving a reagent "S" for blood cell counting; an air hole 27 formed through the top of the container 24; a seal 26 for sealing the air hole 27; and a membrane 25 attached to the bottom of the container 24. The dilution bottle 23 receives the reagent "S" for blood cell counting in the container 24 and is sealed by the seal 26 and the membrane 25. The dilution bottle 23 is not limited to the one shown in FIGS. 3(a) and 3(b). For example, in the dilution bottle 23 shown in FIG. 3c, the lower portion of the container 24 has a reduced diameter, a guide portion 28 is provided such that it extends downward from the membrane 25, and the container 24, the membrane and the guide portion 28 are formed integrally with each other. This dilution bottle 23 is configured such that, when the container 24 is allowed to slide along the bottle guide 19, the guide portion 28 comes into close contact with the outer circumferential side of the capillary 13 such that it can guide the corresponding capillary 13 to the membrane 25. In addition, in this dilution bottle 23, an atmosphere opening portion 261 consisting of, for example, a resin check valve, is provided in the central portion of the seal 26, and when or before the capillary 13 is inserted into and passed through the membrane 25, a ventilation needle (not shown) is inserted into and passed through the atmosphere opening portion 261 such that the inside of the container is ventilated. FIG. 3(c) shows that the container 24, the membrane 25 and the guide portion 28 are formed integrally with each other. However, as shown in FIG. 3(d), the dilution bottle 23 may also be constructed by attaching the membrane 25 to the inlet at the bottom of the container 24 and fitting a separate guide member 281 therewith. In addition, as shown in FIG. 3(e), the dilution bottle 23 may also be constructed such that the reagent "S" for blood cell counting is received in the container 24 by pressing a sphere 29 into the position corresponding to the membrane 25 and such that the sphere 29 is pressed into the container 24 by the capillary 13 in the measurement process so as to open the container 24. The capacity of the container 24 is not specifically limited, because it varies depending on the type of micro blood cell counter or the dilution factor of the reagent "S" for blood cell counting. For example, the capacity of the container 24 may preferably be 0.1-2 ml, more preferably 0.3-1.0 ml, and even more preferably 0.5 ml.

—Body 100—

Figure 4:
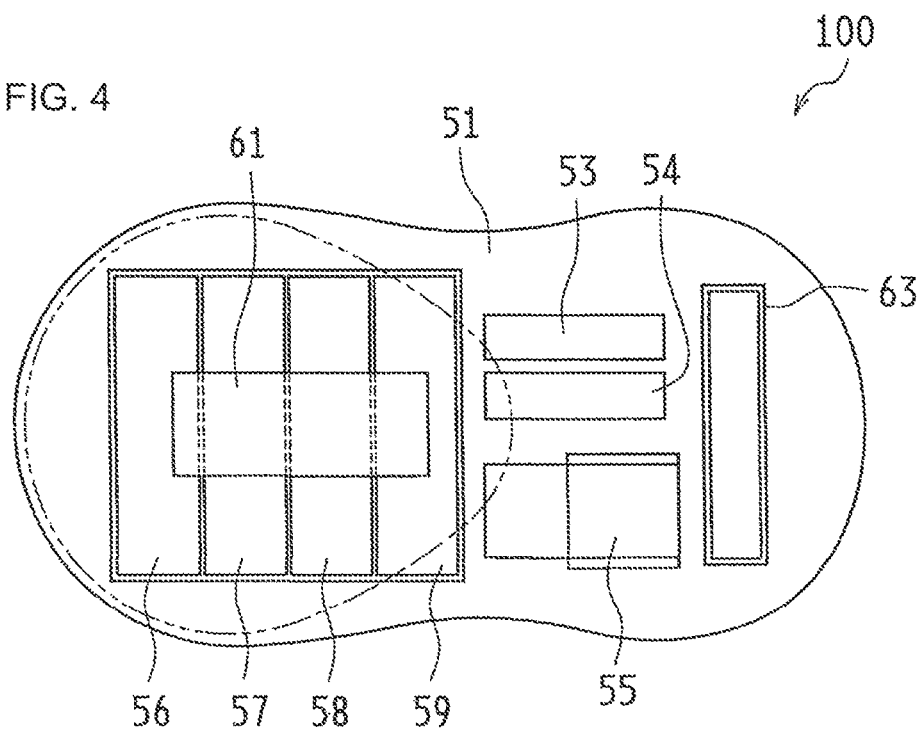
FIG. 4 is a top view showing a body in a micro blood cell counter.
Figure 5:
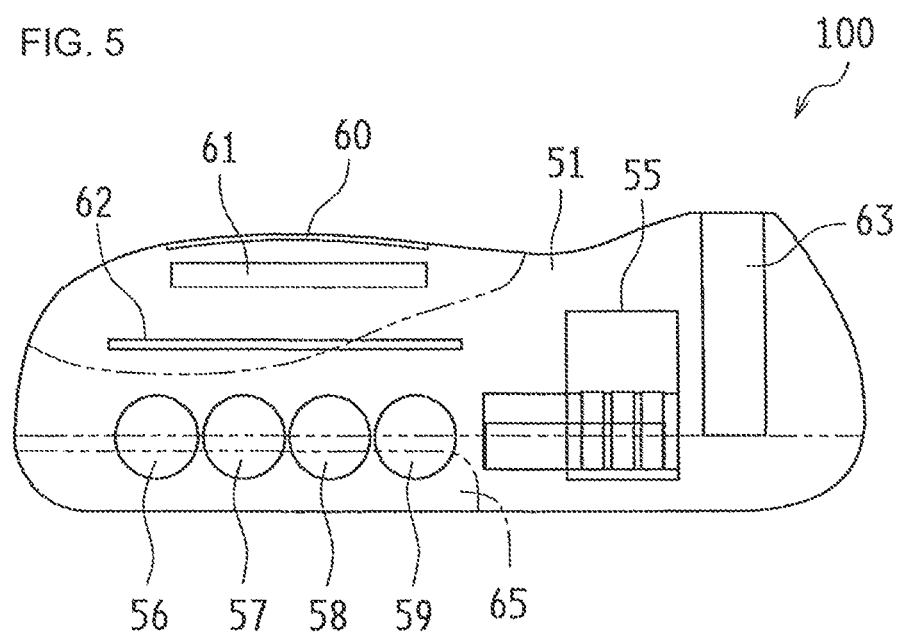
FIG. 5 is a side view showing a body in a micro blood cell counter.

FIGS. 4 and 5 show a body 100 of the micro blood cell counter. The body 100 of the micro blood cell counter is covered with a case 51, and three-way electronic valves 53 and 54, a diaphragm pump 55, batteries 56, 57, 58 and 59, a liquid crystal display (LCD) 61, a circuit board 62 and a cartridge setting portion 63 are provided in the case 51. In addition, a transparent plate 60 is attached in a window frame formed on the top surface of the case 51 such that the display of the LCD 61 can be seen from the outside. In addition, a battery cover 65 which is open or closed in order to set or replace the batteries 56, 57, 58 and 59 is provided over the side and bottom of the case 51.

The discharge (pressure) side of the diaphragm pump 55 is connected to the common port of the three-way electronic valve 53, and the suction (vacuum) side of the diaphragm pump 55 is connected to the common port of the three-way electronic value 54. In addition, the NO port (normally open port) of the three-way electronic valve 53 is connected to the NC port (normally closed port) of the three-way valve 54, and the NC port of the three-way electronic valve 53 is connected to the NO port of the three-way electronic valve 54.

In addition, the line that connects the NO port of the three-way electronic valve 53 with the NC port of the three-way electronic valve 54 is configured such that the pump connection port 17 of the cartridge-type measurement unit 1 is connected thereto when the measurement unit 1 prepared in the form of the cartridge is set in the cartridge-setting portion 63. Operating power is supplied to the three-way electronic valves 53 and 54, the diaphragm pump 55 and the LCD 61 by the batteries 56, 57, 58 and 59, and the three-way electronic valves 53 and 54, the diaphragm pump 55 and the LCD 61 are controlled by a control circuit provide on the circuit board 62. Also, a signal indicating the variation in impedance is supplied to an operational circuit provided on the circuit board 62, whereby blood cells in the blood sample are measured, and the results of the measurement are displayed in the LCD 61.

<Blood Analysis Method of the Present Invention>

Hereinafter, the blood analysis method of the present invention, which uses the micro blood cell counter having the above-described configuration, will be described.

In the blood analysis method of the present invention, a step of collecting capillary blood from a living body is first carried out. In this embodiment, the blood collecting step is carried out by pricking, for example, the fingertip of a subject (living body) with the tip of the capillary and drawing capillary blood (1 µL) into the capillary 13 by a capillary phenomenon.

Then, a step of diluting the collected capillary blood with the reagent "S" for blood cell counting of the present invention is carried out to prepare a blood sample. In this embodiment, in this diluting step, the dilution bottle 23 containing the reagent "S" for blood cell counting is allowed to slide along the bottle guide 19, and the membrane 25 of the dilution bottle 23 is broken at the tip of the capillary 13, whereby the tip of the capillary 13 is inserted into the dilution bottle 23. Then, the seal 26 of the dilution bottle 23 is removed. Thus, the dilution bottle 23 is open to the atmosphere through the hole at the top thereof.

Figure 6:
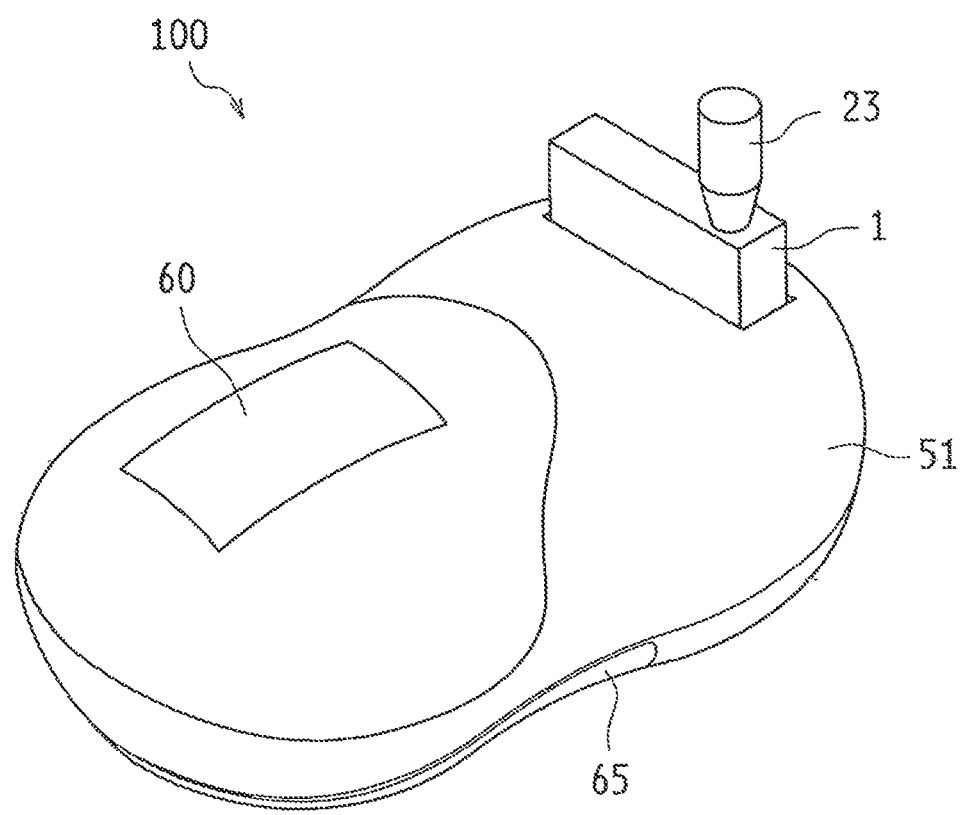
FIG. 6 is a perspective view showing a measurement unit (provided with a dilution bottle) inserted into a body in a micro blood cell counter.

When the measurement unit 1 is inserted and set in the body 100 of the micro blood cell counter (see FIG. 6), the pump connection port 17 is connected to the diaphragm pump 55 accommodated in the body 100 of the micro blood cell counter. Also, the sensor substrate 20 is electrically connected to an impedance measurement circuit provided in the body 100. In addition, when the diaphragm pump 55 is operated to apply pressure to the inside of the capillary 13 through the pump connection portion 17, the fluid path 3 for connection to the outside, the liquid storage cell 7, the fluid path 8, the absorbance-measuring cell 9, the fluid path 10, the detection fluid path 11 and the fluid path 12, the capillary blood in the capillary 13 is then pressure-introduced into the dilution bottle 23. At this time, bubbling occurs in the dilution bottle 23, so that the capillary blood and the reagent "S" for blood cell counting are mixed, thereby obtaining a blood sample diluted with the reagent "S" for blood cell counting (dilution factor: 251).

After the diluting step, a step of counting leukocytes in the blood sample is carried out according to the present invention. In this embodiment, in the counting step, the diaphragm pump 55 is operated to apply a vacuum to the inside of the capillary 13 through the pump connection port 17, the fluid path 3 for connection to the outside, the liquid storage cell 7, the fluid path 8, the absorbance-measuring cell 9, the fluid path 10, the detection fluid path 11 and the fluid path 12. Then, the blood sample in the dilution bottle 23 is introduced into the detection fluid path 11 through the capillary 13 and the fluid path 12. Herein, the variation in impedance between the electrodes 14 and 15 provided in the detection fluid path 11 occurs, and the micro blood cell counter measures particles in the blood sample on the basis of this variation in impedance.

The diluted blood passed through the detection fluid path 11 flows to the absorbance-measuring cell 9 through the fluid path 10. When the amount of hemoglobin is to be measured in addition to the counting of leukocytes, the amount of hemoglobin in the blood sample can be measured by measuring the absorbance of the absorbance-measuring cell 9 with an optical sensor (not shown). In addition, the blood sample passed through the absorbance-measuring cell 9 flows to the liquid storage cell 7 through the fluid path 8 and is collected as waste. After completion of the measuring step, the measurement unit 1 is separated from the body of the micro blood cell unit and wasted together with the blood sample collected in the liquid storage cell 7.

EXAMPLE 1

20 g/L of chloroquine diphosphate as a chloroquine salt and 36.6 g/L of hexadecyltrimethylammonium bromide as a quaternary ammonium salt were dissolved in 0.5M phosphate buffer solution, and sodium chloride as an electrolyte was added thereto, thereby preparing a reagent for cell blood counting according to the present invention, which had an osmotic pressure of 390 Osm/kg. Herein, the osmotic pressure was measured with an osmometer (Osmostat OM-6020; Daiichikagakuco, Kyoto, Japan).

EXAMPLE 2

A reagent for blood cell counting according to the present invention, which had an osmotic pressure of 390 Osm/kg, was prepared in the same manner as Example 1, except that dodecyltrimethyl ammonium chloride (36.6 g/L) was used as the quaternary ammonium.

COMPARATIVE EXAMPLE 1

A reagent for blood cell counting having an osmotic pressure of 390 Osm/kg was prepared in the same manner as Example 1, except that the chloroquine salt was not used.

Figure 7:
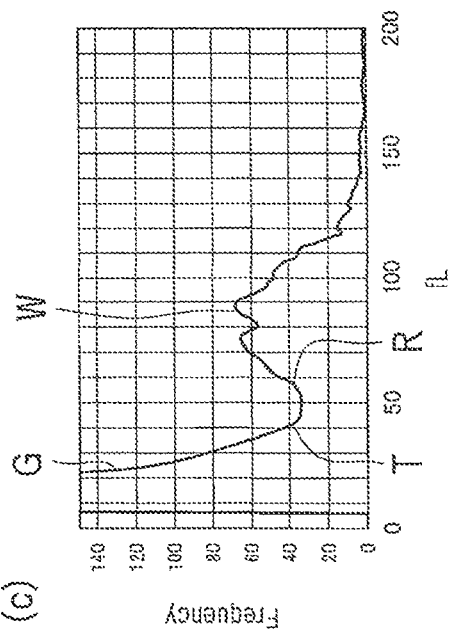
FIGS. 7($a$) and 7($b$) are leukocyte volume histograms obtained by measuring blood samples diluted with the inventive reagents for blood cell counting according to Examples 1 and 2, respectively.
Figure 7:
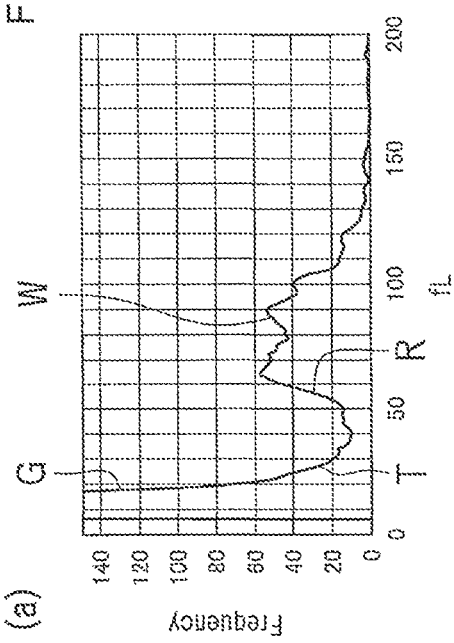
Figure 7:
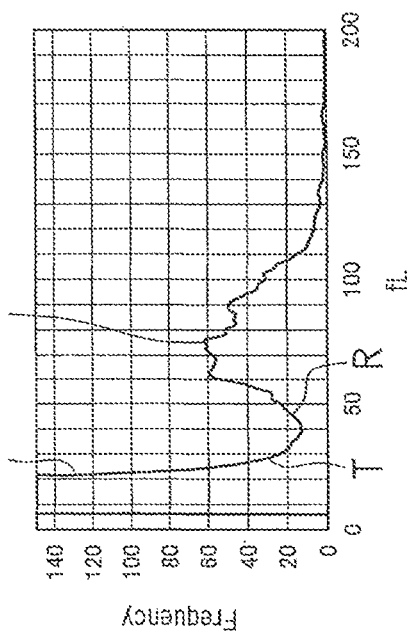
Figure 8:
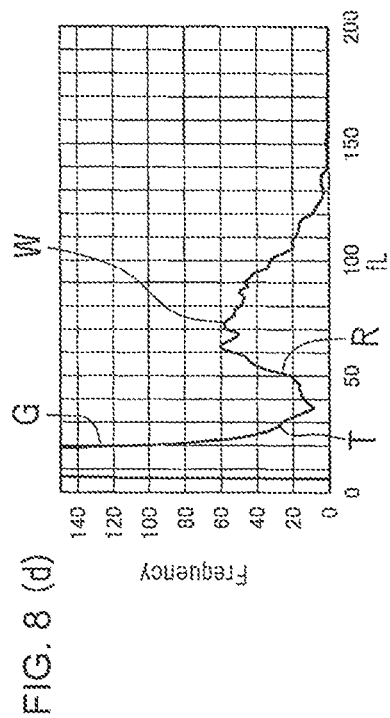
FIGS. 8($a$), 8($b$), 8($c$) and 8($d$) are leukocyte volume histograms obtained by measuring blood samples diluted with the inventive reagents for blood cell counting according to Examples 3, 1, 4 and 5, respectively.
Figure 8:
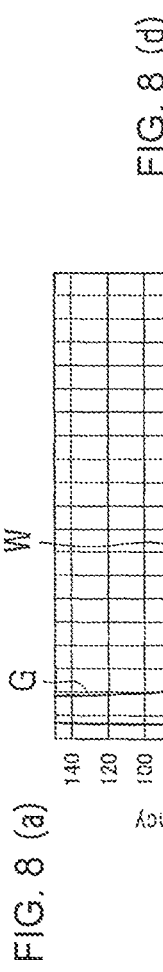
Figure 8:
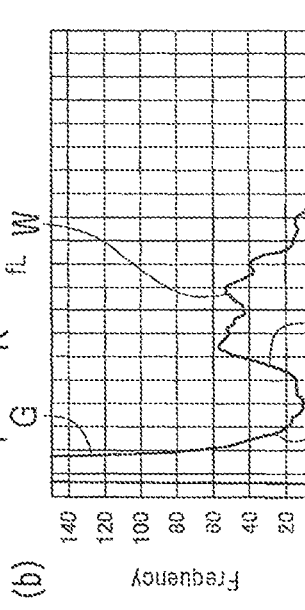
Figure 8:
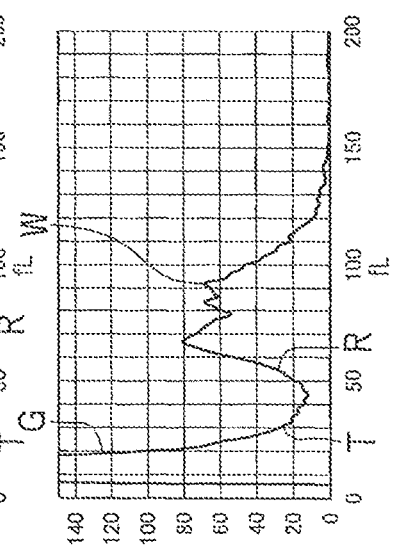

The inventive reagents for blood cell counting according to Examples 1 and 2 and the reagent for blood cell counting according to Comparative Example 1 were placed and sealed in different dilution bottles 23. Then, the fingertip of a subject was pricked with the top of the capillary 13 provided in the measurement unit 1 to draw capillary blood into the capillary 13, and the top of the capillary 13 was inserted into the dilution bottle 23. Then, the measurement unit 1 was inserted into the cartridge-setting portion 63 of the micro blood cell counter, thereby performing the blood analysis method of the present invention. FIGS. 7(a)-7(c) show the leukocyte volume histograms obtained by this analysis method.

The leukocyte volume histograms shown in FIGS. 7(a) and 7(b) were those obtained by measuring the blood samples diluted with the inventive reagents for blood cell counting according to Examples 1 and 2, respectively. In the leukocyte volume histograms shown in FIGS. 7(a) and 7(b), it was seen that the ghost noise "G" and the leukocyte peak "W" were clearly isolated from each other and that platelet aggregates had little or no influence on miscounting. In addition, it was observed that a minimum value of a relative frequency of valleys in distribution where the tailing portion of the ghost peak and the leading portion of the leukocyte peak in the histogram overlap with each other lies within a particle volume range of 35 to 50 fL. Thus, leukocytes in the blood samples can be counted with high accuracy by determining a count start volume within a particle volume range of 35 to 50 fL and counting particles having a volume equal to or larger than the determined count start volume as leukocytes.

Meanwhile, FIG. 7(c) shows a leukocyte volume histogram obtained by measuring the blood sample diluted with the reagent for blood cell counting according to Comparative Example 1. In this leukocyte volume histogram, the ghost peak was significantly larger, and the tailing portion thereof was shifted toward the higher volume side and overlapped with the leading portion of the leukocyte peak over a wide range. Thus, it was found that even when the count start volume is determined within a particle volume range of 35 to 50 fL, miscounting derived from platelet aggregates occurs, resulting in that leukocytes cannot be counted with high accuracy.

EXAMPLES 3 to 5

Reagents for blood cell counting were prepared in the same manner as Example 1, except that the concentration of the chloroquine salt was changed to 10 g/L (Example 3), 40 g/L (Example 4) and 80 g/L (Example 5).

The inventive blood analysis method for measuring capillary blood was carried out using each of the reagents for blood cell counting according to Examples 3 to 5 in addition to the reagent for blood cell counting according to Example 1. FIGS. 8(a)-8(d) shows the obtained leukocyte volume histograms.

FIGS. 8(a), 8(b), 8(c) and 8(d) show leukocyte volume histograms obtained by measuring the blood samples diluted with the inventive reagents for blood cell counting according to Examples 3, 1, 4 and 5, respectively.

As can be seen from the results in FIGS. 8(a)-8(d), when the concentration of the chloroquine salt in the reagent for blood cell counting is 10 g/L or higher, platelet aggregates are dissociated so that the range in which the tailing portion of the ghost peak "G" and the leading portion "R" of the leukocyte peak "W" overlap with each other becomes narrower, suggesting that the influence of the ghost peak on miscounting is substantially eliminated.

EXAMPLES 6 and 7

Reagents for blood cell counting were prepared in the same manner as Example 1, except that the concentration of the quaternary ammonium salt was changed to 10 g/L (Example 6) and 50 g/L (Example 7).

COMPARATIVE EXAMPLES 2 and 3

Reagents for blood cell counting were prepared in the same manner as Example 1, except that the concentration of the quaternary ammonium salt was changed to 5 g/L (Comparative Example 2) and 100 g/L (Comparative Example 3).

The inventive blood analysis method for measuring capillary blood was carried out using each of the reagents for blood cell counting according to Examples 6 and 7 and Comparative Examples 2 and 3 in addition to the reagent for blood cell counting according to Example 1. FIGS. 9(a)-9(e) shows the obtained leukocyte volume histograms.

Figure 9:
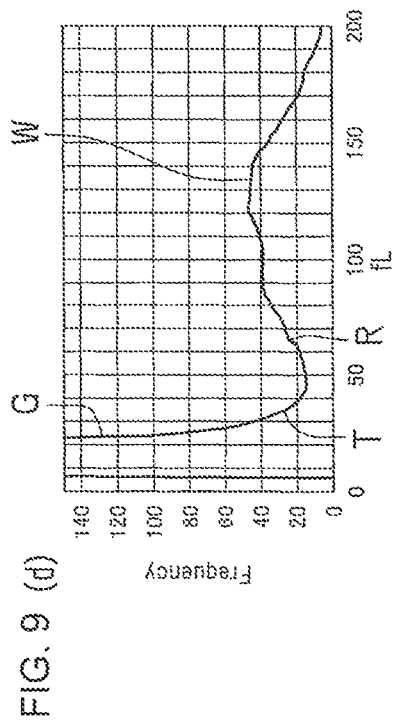
FIGS. 9($a$), 9($b$) and 9($c$) are leukocyte volume histograms obtained by measuring blood samples diluted with the inventive reagents for cell blood counting according to Examples 6, 1 and 7, respectively.
Figure 9:
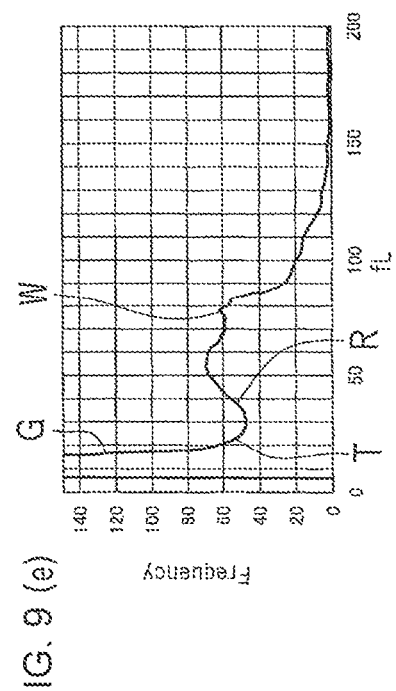
Figure 9:
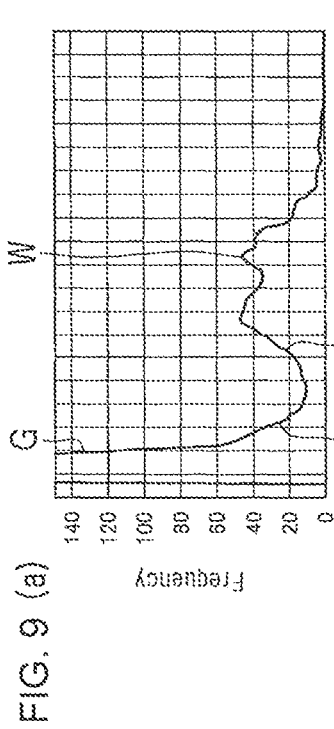
Figure 9:
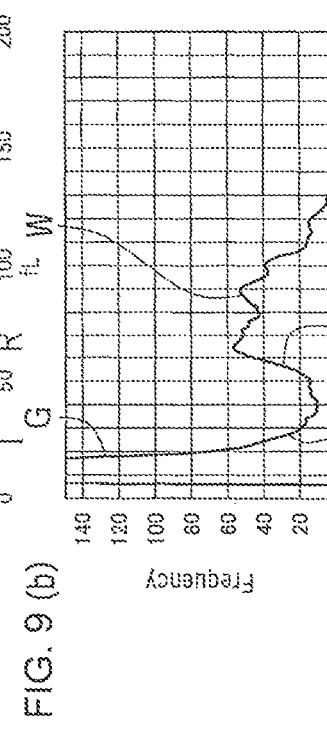
Figure 9:
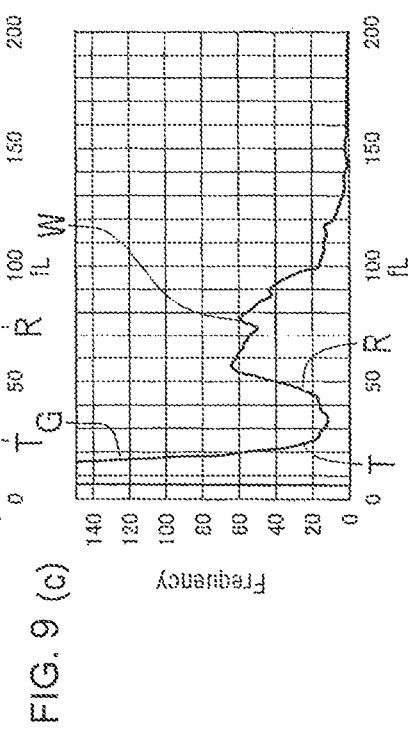
Figure 11:
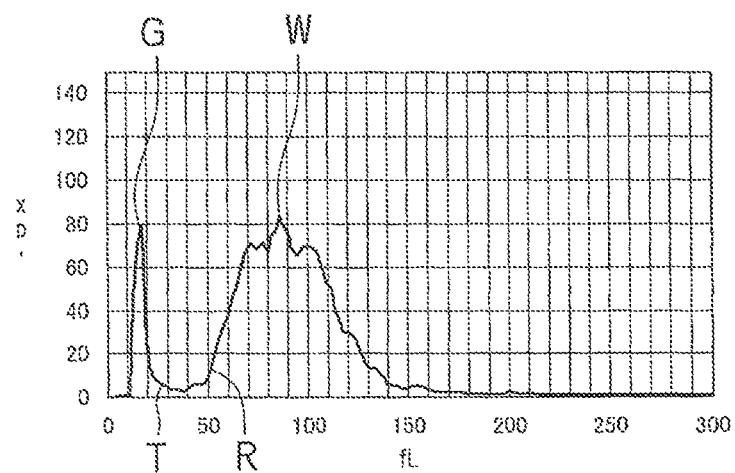
FIG. 11 is a leukocyte volume histogram obtained by measuring a blood sample prepared by diluting venous blood with a reagent for blood cell counting according to the prior art.
Figure 12:
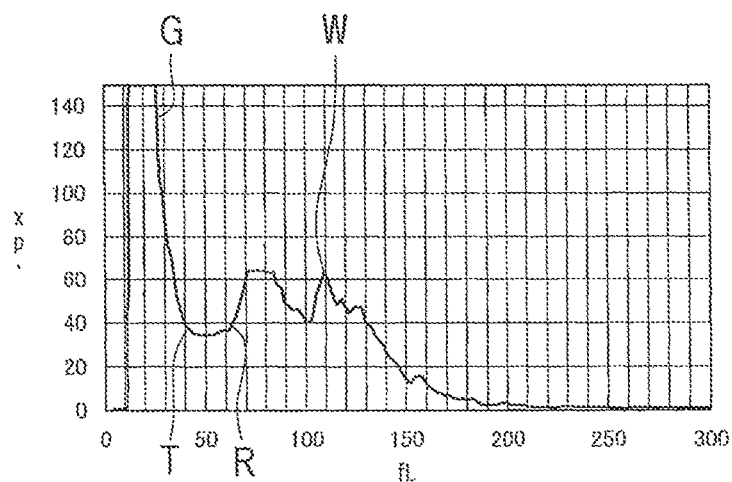
FIG. 12 is a leukocyte volume histogram obtained by measuring a blood sample prepared by diluting capillary blood with a reagent for blood cell counting according to the prior art.

FIGS. 9(a), 9(b) and 9(c) show leukocyte volume histograms obtained by measuring the blood samples diluted with the inventive reagents for blood cell counting according to Examples 6, 1 and 7, respectively. Also, FIGS. 9(d) and 9(e) show leukocyte volume histograms obtained by measuring the blood samples diluted with the inventive reagents for blood cell counting according to Comparative Examples 2 and 3, respectively.

From the results in FIGS. 9(a)-9(e), it was observed that when the concentration of the quaternary ammonium salt in the reagent for blood cell counting was less than 10 g/L, a clear leukocyte peak was not obtained. On the other hand, when the concentration of the quaternary ammonium salt in the reagent for blood cell counting was more than 50 g/L, the leukocyte peak was shifted to the lower volume side, and thus the tailing portion of the ghost peak and the leading portion of the leukocyte peak were widely overlapped with each other.

Thus, it was confirmed that when the concentration of the quaternary ammonium salt in the reagent for blood cell counting is 10-50 g/L, a minimum value of a relative frequency of valleys in distribution where the tailing portion of the ghost peak and the leading portion of the leukocyte peak in the histogram overlap with each other can lie within a particle volume range of 35 to 50 fL.

EXAMPLES 8 and 9

Reagents for blood cell counting according to the present invention were prepared in the same manner as Example 1, except that the osmotic pressures of the reagents were adjusted to 200 Osm/kg (Example 8) and 600 Osm/kg (Example 9) by changing the concentration of NaCl serving as the electrolyte.

COMPARATIVE EXAMPLES 4 and 5

Reagents for blood cell counting were prepared in the same manner as Example 1, except that the osmotic pressures of the reagents were adjusted to 100 Osm/kg (Comparative Example 4) and 1000 Osm/kg (Comparative Example 9) by changing the concentration of NaCl serving as the electrolyte.

The inventive blood analysis method for measuring capillary blood was carried out using each of the reagents for blood cell counting according to Examples 8 and 9 and Comparative Examples 4 and 5 in addition to the reagent for blood cell counting according to Example 1. FIGS. 10(a)-10(e) shows the obtained leukocyte volume histograms.

FIGS. 10(a), 10(b) and 10(c) show leukocyte volume histograms obtained by measuring the blood samples diluted with the inventive reagents for blood cell counting according to Examples 8, 1 and 9, respectively. Also, FIGS. 10(d) and 10(e) show leukocyte volume histograms obtained by measuring the blood samples diluted with the inventive reagents for blood cell counting according to Comparative Examples 4 and 5, respectively.

From the results in FIGS. 10(a)-10(e), it was seen that when the osmotic pressure of the reagent for blood cell counting was less than 200 Osm/kg, a clear leukocyte peak was not obtained. On the other hand, when the osmotic pressure of the reagent for blood cell counting was more than 600 Osm/kg, the leukocyte peak was shifted to the lower volume side, and thus the tailing portion of the ghost peak and the leading portion of the leukocyte peak were widely overlapped with each other.

Thus, it was confirmed that when the osmotic pressure of the reagent for blood cell counting is 200~600 Osm/kg, a minimum value of a relative frequency of valleys in distribution where the tailing portion of the ghost peak and the leading portion of the leukocyte peak in the histogram overlap with each other can lie within a particle volume range of 35 to 50 fL.

The present invention can be carried out in various forms without departing from the sprit or main features thereof. Therefore, the foregoing embodiments are merely exemplary in all points and should not be restrictedly interpreted. The scope of the present invention is defined by the claims and is not restricted by the text of the specification. Further, all modifications, various improvements, substitutions and alterations belonging to the equivalent range of the claims are within the scope of the present invention.

INDUSTRIAL APPLICABILITY

The present invention enables leukocytes in capillary blood to be counted with high accuracy. In addition, the present invention can also be used to analyze other blood components, such as platelets or erythrocytes.

The invention claimed is:

1. A blood analysis method in which blood cells in capillary blood collected from a living body are counted by a particle analyzer, the method comprising:
    collecting capillary blood from the living body;
    diluting the collected capillary blood with an aqueous solution containing a chloroquine salt, thereby preparing a blood sample, wherein the aqueous solution contains a chloroquine salt at a concentration of 10 g/L or more and
    introducing the blood sample into the particle analyzer and counting leukocytes in the blood sample by the particle analyzer.

2. The blood analysis method of claim 1, wherein the aqueous solution containing the chloroquine salt further comprises an electrolyte at a concentration to adjust the osmotic pressure of the aqueous solution containing the chloroquine salt to 200-600 Osm/kg.

3. The blood analysis method of claim 1, wherein the capillary blood is diluted to a sufficient ratio wherein a minimum value of a relative frequency in a region of a leukocyte volume histogram where a tailing portion of a ghost peak and a leading portion of a leukocyte peak overlap with each other lies within a particle volume range of 35 to 50 fL, the leukocyte volume histogram being obtained when the diluted blood sample is introduced into the particle analyzer in the counting step.

4. The blood analysis method of claim 1, wherein diluting the capillary blood is performed with a reagent for blood cell counting comprising an anti-platelet aggregation agent.

5. The blood analysis method of claim 1, wherein counting the leukocytes comprises determining a count start volume in a particle volume range of 35 to 50 fL and counting particles having a volume equal to or larger than the determined count start volume as the leukocytes.

6. The blood analysis method of claim 2, wherein the capillary blood is diluted to a sufficient ratio wherein a minimum value of a relative frequency in a region of a leukocyte volume histogram where a tailing portion of a ghost peak and a leading portion of a leukocyte peak overlap with each other lies within a particle volume range of 35 to 50 fL, the leukocyte volume histogram being obtained when the diluted blood sample is introduced into the particle analyzer in the counting step.

7. The blood analysis method of claim 2, wherein diluting the capillary blood is performed with a reagent for blood cell counting comprising an anti-platelet aggregation agent.

8. The blood analysis method of claim 2, wherein counting the leukocytes comprises determining a count start volume in a particle volume range of 35 to 50 fL and counting particles having a volume equal to or larger than the determined count start volume as the leukocytes.

9. A blood analysis method comprising:
    obtaining blood that has been generated by a wound and which has been exposed to ambient air; then
    diluting the traumatized and air exposed blood into a solution of electrolyte sufficient to adjust osmotic pressure of the solution to 200-600 Osm/kg, and at least 1% by weight chloroquine to facilitate large particle dispersion; and then
    introducing the prepared sample into a particle analyzer that counts leukocytes.

10. The blood analysis method of claim 9, wherein the solution of electrolyte and chloroquine further comprises surfactant at a concentration of 10-50 g/L.

11. The blood analysis method of claim 10, wherein the surfactant comprises an anionic surfactant.

12. The blood analysis method of claim 9, wherein the capillary blood is diluted to a sufficient ratio wherein a minimum value of a relative frequency in a region of a leukocyte volume histogram where a tailing portion of a ghost peak and a leading portion of a leukocyte peak overlap with each other lies within a particle volume range of 35 to 50 fL, the leukocyte volume histogram being obtained when the diluted blood sample is introduced into the particle analyzer in the counting step.

13. The blood analysis method of claim 9, wherein diluting the capillary blood is performed with a reagent for blood cell counting comprising an anti-platelet aggregation agent.

14. The blood analysis method of claim 9, wherein counting the leukocytes comprises determining a count start volume in a particle volume range of 35 to 50 fL and counting particles having a volume equal to or larger than the determined count start volume as the leukocytes.

* * * * *